(12) United States Patent
Pacheco et al.

(10) Patent No.: US 10,647,624 B2
(45) Date of Patent: May 12, 2020

(54) METHOD FOR PRODUCING BUTADIENE FROM BUTANEDIOLS

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Nuno Pacheco, Clermont-Ferrand (FR); Margarita Dorato, Clermont-Ferrand (FR); Marc Jacquin, Lyons (FR); Rejane Dastillung, Lyons (FR); Sophie Couderc, Neuilly sur Seine (FR)

(73) Assignees: IFP Energies nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/063,595

(22) PCT Filed: Dec. 13, 2016

(86) PCT No.: PCT/EP2016/080824
§ 371 (c)(1),
(2) Date: Jun. 18, 2018

(87) PCT Pub. No.: WO2017/102743
PCT Pub. Date: Jun. 22, 2017

(65) Prior Publication Data
US 2018/0370869 A1 Dec. 27, 2018

(30) Foreign Application Priority Data
Dec. 18, 2015 (FR) .................... 15 62859

(51) Int. Cl.
| C07C 1/207 | (2006.01) |
| C07C 67/08 | (2006.01) |
| C07C 51/46 | (2006.01) |
| C07C 1/213 | (2006.01) |
| C07C 51/09 | (2006.01) |
| C07C 51/44 | (2006.01) |
| C07C 11/167 | (2006.01) |
| C07C 69/16 | (2006.01) |

(52) U.S. Cl.
CPC ............ *C07C 1/2078* (2013.01); *C07C 1/213* (2013.01); *C07C 11/167* (2013.01); *C07C 51/09* (2013.01); *C07C 51/44* (2013.01); *C07C 51/46* (2013.01); *C07C 67/08* (2013.01); *C07C 69/16* (2013.01); *Y02P 20/127* (2015.11)

(58) Field of Classification Search
CPC ... C07C 1/20–213; C07C 69/16; C07C 67/08; C07C 11/167; C07C 1/2078; C07C 1/213; C07C 51/09; C07C 51/44; C07C 51/46; C07C 53/08; Y02P 20/127
See application file for complete search history.

(56) References Cited

U.S. PATENT DOCUMENTS

| 2,372,221 A | 3/1945 | Morell |
| 2,383,205 A | 8/1945 | Mattox |
| 5,776,320 A | 7/1998 | Marion |

FOREIGN PATENT DOCUMENTS

| FR | 859902 A | 1/1941 |
| FR | 2737131 A1 | 1/1997 |

OTHER PUBLICATIONS

International Search Report PCT/EP2016/080824 dated May 12, 2017.

*Primary Examiner* — Ali Z Fadhel
(74) *Attorney, Agent, or Firm* — Millen, White, Zelano and Branigan, P.C.

(57) ABSTRACT

The invention relates to a method for producing 1,3-butanediene from a butanediol feedstock that includes:
a) A step for esterification of butanediol by a carboxylic acid to form the corresponding diester;
b) A step for pyrolysis of the diester effluent obtained from step a);
c) A step for distillation fed by at least the carboxylic acid effluent obtained from step a), and producing an aqueous distillate and a carboxylic acid residue;
d) A step for drying the carboxylic acid that is fed at least by the carboxylic acid residue obtained from step c) and producing a water effluent and a carboxylic acid product that feeds step a).

12 Claims, No Drawings

METHOD FOR PRODUCING BUTADIENE FROM BUTANEDIOLS

FIELD OF THE INVENTION

The invention relates to the method for producing 1,3-butadiene from a butanediol feedstock that comprises at least one butanediol selected from the list that consists of 1,4-butanediol, 2,3-butanediol, 1,3-butanediol and mixtures thereof.

PRIOR ART

Today, 95% of the production of 1,3-butadiene is ensured by the steam-cracking of hydrocarbons and the subsequent extraction of diolefins within a $C_4$ distillation fraction by extractive distillation methods.

The variation in cost of the raw materials has led to operating the steam-cracking units with increasingly lighter but less expensive feedstocks, leading to the reduction in the production of the $C_4$ fraction and consequently of 1,3-butadiene.

Other methods make it possible to produce butadiene on the industrial scale. It is possible to cite the methods for dehydrogenation of butenes and butanes, starting from a $C_4$ hydrocarbon resource. It is also possible to mention the Lebedev method, which makes it possible to obtain 1,3-butadiene from ethanol.

Another method for producing 1,3-butadiene was performed on the pilot scale in 1945 in the USA and described in, for example, the patents FR 859902, U.S. Pat. Nos. 2,383,205, 2,372,221, and in *Industrial & Engineering Chemistry*, 37 (9), 1945, pp. 865 to 908. This method consists of two primary steps:

The esterification of 2,3-butanediol by a carboxylic acid to form the corresponding diester The pyrolysis of diester for producing 1,3-butadiene and carboxylic acid, which is recycled in the esterification step.

This method was developed because the direct dehydration of 2,3-butanediol leads to the very large majority formation of methyl ethyl ketone (MEK), and MEK cannot be dehydrated to form 1,3-butadiene. This method is particularly advantageous because the step for pyrolysis of diester can be carried out with very good yields (typically more than 80%), and the 1,3-butadiene that is obtained is of high purity (typically more than 99%), which is crucial for its use in various applications (fine chemistry, elastomer).

A problem raised by the method for producing 1,3-butadiene from one of the isomers of butanediol (1,4-butanediol, 2,3-butanediol, and 1,3-butanediol) by esterification and then pyrolysis is the purification of carboxylic acid for the purpose of its recycling. The heterogeneous azeotropic distillation used to dry the carboxylic acid, i.e., to eliminate the water that is produced in the esterification step, is difficult to perform, in particular because of the accumulation of organic compounds in the carboxylic acid.

Actually, these organic compounds, by accumulating in the carboxylic acid, disrupt the liquid-liquid balances of the water/carboxylic acid/driver system and even homogenize a system that is two-phase in their absence, and therefore make the drying of the carboxylic acid by heterogeneous azeotropic distillation inoperable.

The organic compounds in question can be:

Dehydration by-products of butanediols (THF for a 1,4-butanediol feedstock, MEK for a 2,3-butanediol feedstock, and 1-buten-4-ol for a 1,3-butanediol feedstock) formed in particular in the esterification step;

Intermediate pyrolysis compounds and by-products formed in the pyrolysis step (such as, for example, vinylcyclohexene, methyl vinyl carbinol acetate (MVCA), methyl ethyl ketone enol acetate (MEKEA), crotyl acetate (CA), VCH, MEK or methyl acetylacetone (MAA)), which are difficult to separate from the carboxylic acid that is released in the pyrolysis step, and which can therefore be totally or partially sent back to the esterification step.

These numerous intermediate pyrolysis compounds have a boiling point that is close to that of acetic acid and form homogeneous azeotropes (maximum and minimum) with the latter. The purification of acetic acid therefore cannot be done by simple distillation. The U.S. Pat. No. 2,372,221 describes the use of pyrolytic liquid without prior purification directly in the esterification step, and the catastrophic consequences on the heterogeneous azeotropic distillation used (driver=benzene in this case) for drying the carboxylic acid.

In the method of the prior art (*Industrial & Engineering Chemistry*, 37 (9), 1945, pp. 865 to 908), the drying of the acetic acid that is introduced in excess in the esterification step is carried out with a variant of the heterogeneous azeotropic distillation that is well known to one skilled in the art, in which a distillation column makes it possible to eliminate the MEK and the other organic compounds that accumulate in the driver.

The esterification of butanediol by acetic acid is implemented in a reactive distillation column. The diester is drawn off at the bottom of the column while the excess acetic acid and the water that is produced by the esterification reaction are recovered in the distillate.

A first distillation column is fed by this distillate that essentially consists of acetic acid, water, but also MEK and other organic compounds. The residue of this first column consists of dry and pure acetic acid, with the latter being sent back to the step for esterification of 2,3-butanediol. The distillate from this first distillation column, a mixture that consists of driver (in this case, isopropyl acetate), acetic acid, water and MEK and other organic compounds is drawn off and sent into a decanter.

This decanter makes it possible to separate an aqueous phase that for the most part contains water, and an organic phase that for the most part contains the driver.

The aqueous phase that is obtained from the decanter is sent as reflux from a second distillation column. At the bottom of this second column, clear water, i.e., without driver, is obtained and eliminated from the method. At the top of this second distillation column, the heterogeneous azeotrope that consists of water and driver is recovered and sent back to the decanter.

The organic phase that is obtained from the decanter feeds a third distillation column as reflux. This third column makes it possible to produce at the top the MEK and organic compounds that are eliminated from the method and at the bottom a mixture of driver, water and acetic acid that is sent back as reflux into the first distillation column.

This approach, to be operable, assumes that the third distillation column is extremely effective and keeps the amount of MEK and other organic compounds in the system at a level such that it does not disrupt the liquid-liquid balances in the decanter. However, the liquid-vapor balances between the MEK and the isopropyl acetate are such that it is difficult to envision a good separation of the MEK and the driver, even with a large number of theoretical distillation plates. Other drivers that can be separated more easily from the MEK, such as, for example, butyl acetate, have been considered. Nevertheless, the latter does not make it possible to separate water and acetic acid effectively. In conclusion, it is difficult to find a driver that makes possible both a good separation of water and acetic acid and that can be easily separated from the MEK.

This invention makes it possible to eliminate the problem of accumulation of dehydration by-products of butanediol in carboxylic acid, in a method for producing butadiene from butanediol by esterification and then pyrolysis. In addition, this invention is also applicable for a method for producing butadiene from various butanediol isomers. Actually, the applicant discovered that a particular concatenation of distillation columns could be implemented to eliminate in an effective manner the water that is produced in the esterification step and the organic compounds that can accumulate in carboxylic acid.

The applicant discovered that his invention for drying carboxylic acid and eliminating the organic compounds was particularly robust and could be implemented even if the pyrolytic liquid was recycled without purification prior to the esterification step. In addition, the applicant discovered that the fact of using the pyrolytic liquid without purification prior to the esterification step according to his invention made it possible for the intermediate pyrolysis compounds and the by-products formed in the pyrolysis step not to accumulate in the carboxylic acid.

Thus, the applicant discovered that a particular concatenation of distillation columns, by judicious management of the separations of by-products and the addition of the driver used in the azeotropic distillations, different from that of the method of the prior art, could be implemented for:

Drying the carboxylic acid and recycling it in the esterification step

Eliminating water in an effective manner

Ensuring effective elimination of the dehydration by-products regardless of the butanediol used in the feedstock (2,3-butanediol, 1,4-butanediol, and/or 1,3-butanediol)

Eliminating the intermediate pyrolysis compounds and the pyrolysis by-products of the 2,3-butanediol diester, the 1,4-butanediol diester, and the 1,3-butanediol diester.

The invention therefore makes it possible to simplify the method according to the prior art and thus to reduce the operating costs and investment costs, while maintaining flexibility in the nature of the butanediol feedstock that feeds the method (1,4-butanediol, 2,3-butanediol, 1,3-butanediol and mixtures thereof).

OBJECT AND ADVANTAGE OF THE INVENTION

The invention relates to a method for producing 1,3-butadiene from a butanediol feedstock that comprises at least:
   a) A step for esterification of butanediol by a carboxylic acid to form the corresponding diester, fed by said butanediol feedstock and by a carboxylic acid feed comprising a carboxylic acid feedstock and the liquid pyrolysis effluent obtained from step b), and producing at least a carboxylic acid effluent and a diester effluent, implemented in reactive distillation in the presence of a homogeneous or heterogeneous acid catalyst, operated at a pressure of between 0.01 and 1 MPa;
   b) A step for pyrolysis of the diester effluent obtained from step a) that comprises a reaction section and a separation section and that produces at least a liquid pyrolysis effluent that comprises at least 50% by weight of carboxylic acid and a vapor pyrolysis effluent that comprises more than 90% by weight of butadiene, with said reaction section being operated at a temperature of between 500 and 650° C., the effluent of said reaction section being cooled to a temperature that is less than 100° C. before feeding said separation section;
   c) A step for distillation fed by at least the carboxylic acid effluent obtained from step a), operated in a distillation column at a pressure that is at most equal to 1 MPa, with a temperature at the top of the column of between 0 and 110° C. and a temperature at the bottom of the column of between 100 and 120° C., and that produces an aqueous distillate and a carboxylic acid residue;
   d) A step for drying the carboxylic acid that is fed at least by the carboxylic acid residue obtained from step c) and that produces a water effluent and a carboxylic acid product that feeds step a).

One advantage of the invention is the possibility of treating all of the isomers of butanediol (1,4-butanediol, 2,3-butanediol, 1,3-butanediol and mixtures thereof) to produce 1,3-butadiene with a high yield, greater than 70%.

Another advantage of the invention is the capacity to eliminate the various dehydration by-products of the butanediols, intermediate pyrolysis compounds and pyrolysis by-products with a reduced amount of equipment, thus reducing the operating costs, reducing the investment costs, and increasing the flexibility of the method relative to the feedstock.

DETAILED DESCRIPTION OF THE INVENTION

Feedstock

In accordance with the invention, the method is fed with a butanediol feedstock that comprises at least butanediol, advantageously at least 90% by weight of butanediol. Said butanediol is an isomer of the butanediol that is selected from the list that consists of 1,4-butanediol, 2,3-butanediol, 1,3-butanediol and mixtures thereof. Said butanediol feedstock can also comprise water. Said butanediol feedstock can stem from a method for fermenting sugars or synthesis gas. Said butanediol feedstock can stem from a method for synthesis of butanediol from acetylene and formaldehyde.

Preferably, for the requirements of the invention, the carboxylic acid is acetic acid.

Step a) for Esterification of Butanediol

In accordance with the invention, the method for producing 1,3-butadiene comprises a step a) for esterification of butanediol by a carboxylic acid for forming the corresponding diester fed at least by said butanediol feedstock and by a carboxylic acid feedstock and producing at least a carboxylic acid effluent and a diester effluent, used in reactive distillation in the presence of a homogeneous or heterogeneous acid catalyst, preferably heterogeneous.

This esterification step can be carried out by any implementation of reactive distillation that is well known to one skilled in the art.

The butanediol feedstock is introduced into the upper part of the reactive distillation, and with the carboxylic acid feed comprising the carboxylic acid feedstock, the liquid pyrolysis effluent obtained from step b), advantageously also the carboxylic acid product obtained from step d), is introduced into the lower part of the reactive distillation.

Said reactive distillation is performed at a pressure of between 0.01 and 1 MPa, in a preferred manner at a pressure that is slightly greater than 0.1 MPa. The temperature of the reactive distillation is between the boiling point of the water produced at the top and that of the diester produced at the bottom. In the case where the carboxylic acid that is used is acetic acid, the temperature between the top and the bottom of the reactive distillation typically varies between 100 and 230° C.

At the top, the reactive distillation produces a distillate that constitutes the carboxylic acid effluent. Said carboxylic acid effluent primarily comprises the water that is produced by the esterification reaction, the carboxylic acid that is introduced in excess, and the dehydration by-products that are generated. Said carboxylic acid effluent can also comprise organic impurities coming from the liquid pyrolysis effluent obtained from step b) that is fed in a mixture with the carboxylic acid feedstock.

At the bottom, the reactive distillation produces a residue that constitutes the diester effluent and that primarily comprises the butanediol diester that is produced.

Said esterification step a) is performed in such a way that the conversion of butanediol into butanediol diester is greater than 95 mol %, preferably greater than 99 mol %. These performances are achieved by adjusting the operating parameters of the reactive distillation, such as the reflux and reboiling rates, and the butanediol feedstock/carboxylic acid feedstock ratio of said step a), as known by one skilled in the art.

The flow rates of butanediol feedstock and carboxylic acid feed are adjusted in such a way that the carboxylic acid/diol molar ratio at the input of the esterification step is between 2 and 6, preferably between 2 and 4, and in a very preferred manner between 2 and 3.5.

The molar reflux rate (equal to the reflux molar flow rate of the condenser toward the top of the column divided by the distillate molar flow rate) is between 0.5 and 10, in a preferred manner between 0.5 and 4, and in a very preferred manner between 1 and 2. In accordance with the invention, the molar reboiling rate (equal to the reflux molar flow rate of the reboiler toward the bottom of the column divided by the residue molar flow rate) is between 0.5 and 10, in a preferred manner between 4 and 10, and in a very preferred manner between 5 and 6.

In a preferred arrangement, said reactive distillation comprises a mixed reaction/separation zone located between two separation zones.

In this arrangement, said butanediol feedstock is introduced into said reactive distillation column in an intermediate stage, preferably between the mixed zone and the separation zone located above the mixed zone. Said carboxylic acid feed is introduced into said reactive distillation column in one or more intermediate stages located below the injection stage of the butanediol feedstock. In a preferred manner, said carboxylic acid feedstock is introduced into the reactive distillation column in a single intermediate stage, located between the mixed zone and the separation zone located below.

Intermediate stage is defined as a stage of the reactive distillation column that is neither the reboiler nor the condenser. Above or upper is defined as facing toward the condenser. Below or lower is defined as facing toward the reboiler.

Each of said separation zones comprises internals that are known to one skilled in the art, such as plates, random packing or structured packing, or a combination of these types of internals, with said internals or said combination having overall an effectiveness of separation for each of said separation zones of at least two theoretical stages, preferably between two and ten theoretical stages, and in a preferred manner between two and four theoretical stages, in such a way as to ensure minimal yield and purity of the diol diester that is produced.

Preferably, said mixed zone comprises a heterogeneous acid catalyst. In a first particular arrangement, said mixed zone consists of plates and catalytic sections, which are located outside of the distillation column, with each catalytic section being connected to the plates of said mixed zone by means of a liquid draw-off on a plate of said mixed zone, with reinjection into the lower plate after passage into said catalytic section. Said mixed zone advantageously comprises at most 20, preferably at most 15, catalytic sections.

In a second particular arrangement, said mixed zone consists of internals that hold said catalyst. Said catalyst is then held in said mixed zone by the means that are known to one skilled in the art. In a non-limiting manner, the heterogeneous catalyst can be held between the plates of a structured packing, be imprisoned in metal grids deposited on the distillation plates, be imprisoned in a fabric shaped in such a way as to serve as packing and to establish the transfer between the gas phase and the liquid phase, or else in a device for particular distribution of liquid and vapor phases as described in the patent FR 2,737,131. In a preferred manner, said mixed zone uses the device for particular distribution of the liquid and vapor phases as described in the patent FR 2,737,131. This device is preferred because it generates a smaller loss of feedstock within the column, with the gas phase being short-circuited by the catalytic zone. This device therefore makes it possible to maintain lower pressure at the bottom of the column and therefore a lower temperature. When a device for particular distribution of liquid and vapor phases as described in the patent FR 2,737,131 is used to hold the heterogeneous catalyst in the column, the mixed zone consists of alternating reaction sections and separation sections. In an advantageous manner, said mixed zone comprises, according to this embodiment, at most 20, preferably at most 15, reaction sections.

The dwell time of the liquid phase in each catalytic section according to the first particular arrangement, or in each reaction section in the second particular arrangement, is advantageously between 5 and 30 minutes, in a preferred manner between 15 and 25 minutes. In addition, the surface velocity of the liquid phase within the fixed catalyst bed is advantageously between 0.05 and 0.5 cm/s, and in a preferred manner between 0.1 and 0.3 cm/s.

Independently of the embodiment, the heterogeneous acid catalyst is selected from among an ion-exchange acid resin (such as Amberlyst, Amberlite, Dowex, and in particular an Amberlyst 35, an Amberlyst 36, or an Amberlyst 70), a mixed oxide ($ZrO_2$, $SnO$) or an acid zeolite (H-MOR, H-MFI, H-FAU, and H-BEA). In a preferred manner, said heterogeneous acid catalyst is stable at a temperature that is higher than 130° C., in a preferred manner higher than 150° C., and in a very preferred manner higher than 170° C.

The acid catalysts that are used to catalyze the esterification reaction also activate the dehydration reactions, in particular at the operating temperatures of said step a), producing MEK or THF or 2-buten-1-ol depending on the butanediol isomer that is present in the butanediol feedstock.

The dwell time in said reactive distillation column, defined as the volume of the reactive distillation divided by the volumetric flow rate of said diol feedstock and said carboxylic acid feedstock, is advantageously between 0.5 h and 10 h, preferably between 0.5 h and 5 h, and in a preferred manner between 1 h and 2 h.

In a preferred manner, the MMH (mol per mol per hour, corresponding to the diol molar flow rate in the diol feedstock divided by the number of moles of catalyst present within said mixed zone) is between 0.05 and 25 h-1, preferably between 0.15 and 20 h-1.

Step b) for Pyrolysis of Butanediol Diester

In accordance with the invention, the method for producing 1,3-butanediene comprises a step b) for pyrolysis of the diester effluent obtained from step a), comprising a reaction section and a separation section and producing at least a liquid pyrolysis effluent comprising at least 50% by weight of carboxylic acid and a vapor pyrolysis effluent comprising more than 90% by weight of butadiene, with said reaction section being operated at a temperature of between 500 and 650° C., with the effluent of said reaction section being cooled to a temperature of less than 100° C. before feeding said separation section.

The pyrolysis reaction transforms 1 mol of butanediol diester into 1 mol of 1,3-butadiene and thus releases 2 mol of carboxylic acid. More than 70 mol % of butanediol diester is converted into 1,3-butadiene. Preferably, more than 80 mol % of butanediol diester is converted into 1,3-butadiene. Said pyrolysis reactor is operated at a temperature of between 500 and 650° C., preferably between 550 and 600° C., and in a preferred manner between 575 and 585° C. The optimal contact time within said reactor is based on the partial pressure of the butanediol diester injected into said reactor. It is typically 1 second for a partial pressure of diol diester of 0.1 MPa and 7 seconds for a partial pressure of diol diester of 0.04 MPa.

Said pyrolysis step b) according to the invention also comprising at least one separation section fed by said pyrolysis effluent, cooled to a temperature of less than 100° C., so as to produce at least a liquid pyrolysis effluent and a vapor pyrolysis effluent that can be easily separated within a gas-liquid separator tank. The pyrolysis effluent obtained from said pyrolysis reactor is cooled quickly to a temperature of less than 100° C., preferably less than 50° C., in such a way as to limit the formation of degradation products by, for example, Diels-Alder reaction of 1,3-butadiene on itself to form vinylcyclohexene (VCH).

Said vapor pyrolysis effluent comprises more than 90% by weight, preferably more than 95% by weight, of 1,3-butadiene (without considering the optional inert diluent used to lower the partial pressure of butanediol diester within the pyrolysis reactor). Said vapor pyrolysis effluent can also contain light organic compounds, obtained from the pyrolysis of the carboxylic acid, such as, for example, in the case where the carboxylic acid is acetic acid, methane, carbon monoxide, carbon dioxide, ketene, hydrogen, or else ethane. Said vapor pyrolysis effluent can be compressed and/or cooled in such a way as to condense 1,3-butadiene. The non-condensable organic compounds obtained from the pyrolysis of carboxylic acid are thus eliminated at the top of a gas-liquid separator in the form of an effluent of light compounds. The 1,3-butadiene can then undergo one or more final purification steps that are well known to one skilled in the art. It is possible to cite in a non-limiting manner the purification on a sieve or on a clay, or else a washing with water. This makes it possible to eliminate the last traces of impurities and to obtain a 1,3-butadiene effluent, which comprises more than 99%, in a preferred manner more than 99.5%, of 1,3-butadiene, which is the product of the method.

Said liquid pyrolysis effluent consists of, for the most part, carboxylic acid. For the most part is defined as at least 50% by weight, and preferably at least 70% by weight. It can also comprise other organic compounds, such as, for example, unconverted butanediol diester, intermediate pyrolysis compounds (i.e., butanediol diester molecules that have lost one carboxylic acid fragment of the two that are required for 1,3-butadiene to form), and optional pyrolysis by-products. The nature of these by-products depends, of course, on the nature of the feedstock that is introduced into the pyrolysis reactor. Numerous intermediate pyrolysis compounds and impurities are produced. By way of illustration, in the case where acetic acid is used for carrying out the esterification of 2,3-butanediol in step a), the liquid pyrolysis effluent comprises 2,3-butanediol diacetate (1.5% by weight), intermediate pyrolysis compounds such as methyl vinyl carbinol acetate (MVCA, 0.8% by weight), methyl ethyl ketone enol acetate (MEKEA, 2.4% by weight), and crotyl acetate (CA, 3.3% by weight) and by-products such as VCH (2.2% by weight), MEK (1.4% by weight), or methyl acetylacetone (MAA, 0.9% by weight). The liquid pyrolysis effluent therefore contains numerous intermediate pyrolysis compounds having a boiling point that is close to that of acetic acid and forming homogeneous azeotropes (maximum and minimum) with the latter. The purification of acetic acid before it is recycled into the esterification step therefore cannot be done by simple distillation.

In a first variant of the invention, the liquid pyrolysis effluent is purified before being recycled to the esterification step a) in a mixture with the carboxylic acid feedstock. This purification makes it possible to eliminate the intermediate pyrolysis compounds and pyrolysis by-products formed in step b).

The liquid pyrolysis effluent is purified by any method that is well known by one skilled in the art. It can be purified by, for example, heterogeneous azeotropic distillation by using water as a driver, as described in the document "*Pilot-Plant Conversion of 2,3-Butylene Glycol Diacetate to 1,3-Butadiene*" in the journal "*Industrial and Engineering Chemistry*," Volume 37, No. 9.

In a second embodiment of the invention, the liquid pyrolysis effluent is directly recycled to the esterification step a) in a mixture with the carboxylic acid feedstock, without purification. The butanediol diester that is not converted at the end of the pyrolysis step b) is thus recovered at the bottom of said reactive distillation column and sent back to the feed of said pyrolysis step b), improving the overall yield of 1,3-butadiene of the method.

In this second embodiment of the invention, the intermediate pyrolysis compounds and certain pyrolysis by-products that are difficult to separate from the carboxylic acid are converted totally or partially under the operating conditions of the esterification step a) into other products that can be separated more easily from the carboxylic acid and that are evacuated at the top of said reactive distillation column to the distillation step c). For example, in the case where the carboxylic acid that is used is the acetic acid for esterifying 2,3-butanediol, the methyl acetylacetone (MAA) and the methyl acetylacetone (MEKEA) that are formed in the pyrolysis step b) are hydrolyzed under the conditions of step a) for esterification of acetic acid and MEK, which are evacuated at the top of said reactive distillation column to the distillation step c).

Distillation Step c)

In accordance with the invention, the distillation step c) is fed by the carboxylic acid effluent that is obtained from step a). The distillation step c) produces an aqueous distillate that comprises the by-products of dehydration and pyrolysis and that does not comprise more than 10% by weight of carboxylic acid that is eliminated from the method and a carboxylic acid residue that is dried in step d).

The feed for step c) comprises the water produced by the esterification reaction, carboxylic acid and organic compounds that are obtained from the dehydration of the butanediol feedstock, such as, for example, THF or MEK or 2-buten-1-ol. Said feed can also comprise intermediate pyrolysis compounds, pyrolysis by-products that are formed in the pyrolysis step b), recycled and not converted in the esterification step a), as well as organic compounds that are obtained from the conversion of the intermediate pyrolysis compounds and pyrolysis by-products in the esterification step a).

Said distillation step c) is performed in a distillation column at a pressure that is at most equal to 1 MPa, and preferably at a pressure of between 0.1 and 0.2 MPa. The temperature of the top of the column is between 0 and 110° C., preferably between 50° C. and 100° C. Under these conditions, the aqueous distillate that is produced at the top of said distillation column consists for the most part of water and organic by-products. For the most part means that the carboxylic acid content does not exceed 10% by weight, preferably does not exceed 5% by weight. The temperature of the bottom of the column is between 100 and 120° C., preferably between 100° C. and 115° C. Thus, the carboxylic acid residue that is produced at the bottom of this first column is low in organic by-products and primarily consists of water and carboxylic acid.

Surprisingly enough, the arrangement of the esterification step a) and the pyrolysis step b) with recycling of the liquid pyrolysis effluent that is obtained from step b) to said step a) leads, because of the various reactions that take place in step a) and step b), to the production of a carboxylic acid effluent that is obtained from step a), able to be separated, on the one hand, into an aqueous distillate that comprises water and the by-products of dehydration and pyrolysis, and, on the other hand, a carboxylic acid residue that consists of water and carboxylic acid.

The carboxylic acid residue that is produced at the bottom of this column has no organic compounds and consists of water and acetic acid. It constitutes the feedstock of step d). This operating mode of the column makes it possible to eliminate more than 98% of the organic by-products and to limit the losses of acetic acid between 0 and 10% by mass, preferably between 0 and 5%, and in a very preferred manner between 0 and 1% by mass.

Based on the butanediol isomer or isomers present in said butanediol feedstock, separation may occur in the condenser of the distillation column used in the distillation step c). In the case where separation occurs, one skilled in the art can increase the reflux rate so as to be outside of the separation zone and to produce a homogeneous mixture again. However, in an advantageous arrangement where separation occurs, the aqueous phase is sent back as reflux to the column and the phase that is rich in organic compounds is drawn off as distillate.

Step d) for Drying Carboxylic Acid

In accordance with the invention, a step d) for drying carboxylic acid is fed by the carboxylic acid residue obtained from the distillation step c) and produces a water effluent and a carboxylic acid product.

Said drying step d) is a water/carboxylic acid separation and can be implemented by, for example, heterogeneous azeotropic distillation in the presence of a driver.

The driver that forms a heteroazeotrope with the carboxylic acid-water mixture is preferably selected from the group that consists of alkanes, aromatic compounds, ketones, esters, and the mixtures of the latter. Preferably, the driver is selected from the group that consists of n-dodecane, mesitylene, 3-pentanone, 2-hexanone, 4-methyl-2-pentanone, 2-pentanone, cyclopentanone, cyclohexanone, diisobutyl ketone, isopropyl acetate, n-propyl acetate, ethyl acetate, n-butyl acetate, isobutyl acetate, and the mixtures of the latter.

According to a preferred arrangement, step d) comprises, at the output of the azeotropic distillation, a step for decanting the water-carboxylic acid-driver mixture, making it possible to separate the aqueous phase (water) from the organic phase comprising the driver and the carboxylic acid, with the organic phase being sent back into the azeotropic distillation column. This preferred arrangement is particularly suitable in the case where the driver is very slightly water-miscible. Preferably, in particular when the carboxylic acid is acetic acid, the driver is isopropyl acetate.

According to another preferred arrangement, regardless of the carboxylic acid and the driver, it is possible to use a distillation column at the output of the decanter to separate the driver that has remained in the aqueous phase during the decanting, with this driver being sent back into the decanter.

The carboxylic acid product is recycled to the esterification step a) in a mixture with the carboxylic acid feedstock.

EXAMPLES

Example 1 [For Comparison] Drying of the Acetic Acid by Heterogeneous Azeotropic Distillation and Elimination of the MEK This example shows that an arrangement according to the prior art, in which a driver is added to the carboxylic acid effluent obtained from the esterification step, with this driver able to be easily separated from the carboxylic acid, poses problems as far as the MEK/driver separation is concerned.

A carboxylic acid effluent obtained from an esterification step conducted in a reactive distillation feeds a heterogeneous azeotropic distillation column. The driver that is used is isopropyl acetate. This carboxylic acid effluent contains MEK, acetic acid, and water. The driver is added to the feedstock.

The heterogeneous azeotropic distillation column is operated at atmospheric pressure, with 30 theoretical stages a reboiling rate by mass of 7.57. The feeding is carried out in the upper third of the column.

The organic phase of the condenser of this column is drawn off and contains 96.2% of the MEK fed into said column as well as the driver. This organic phase feeds a second column that is intended to separate the MEK from the driver.

This separation is very difficult because the dew line and bubble curves of the MEK/isopropyl acetate mixture are very close together, and a very large number of stages (more than 50 theoretical stages) are necessary.

TABLE 1

Material Balance in the Heterogeneous Azeotropic Distillation Column for Drying Acetic Acid According to the Prior Art

|  | Feed | Residue | Organic Phase Condensate | Aqueous Phase Condensate |
|---|---|---|---|---|
| Temperature (° C.) | 94.7 | 115.1 | 112.4 | 112.4 |
| Mass Flow Rate |  |  |  |  |
| MEK | 0.106 | 0.00 | 0.102 | 3.73E−03 |
| Acetic Acid | 1.00 | 0.599 | 0.334 | 0.066 |
| Water | 0.52 | 7.24E−03 | 0.209 | 0.307 |
| Isopropyl Acetate | 1.81 | 0.00 | 1.80 | 5.74E−04 |

Example 2 [Compliant] Recycling of the Liquid Pyrolysis Effluent to Esterification This example shows that the concatenation of the esterification and pyrolysis steps, with recycling of the liquid pyrolysis effluent, leads to the transformation of certain pyrolysis by-products into products that can be easily separated (MEK) in the steps for separation of the carboxylic acid effluent according to the invention. These by-products would otherwise have required dedicated treatment. There is thus synergy between the esterification/pyrolysis concatenation and the recycling of the liquid pyrolysis effluent and the concatenation of separation steps fed by the carboxylic acid effluent according to the invention.

This example shows the possibility of recycling the liquid pyrolysis effluent according to the invention.

A butanediol feedstock that consists of 2,3-butanediol feeds an esterification step. The diester effluent comprises the 2,3-butanediol diacetate that is formed.

The diester effluent feeds a pyrolysis step, which comprises a pyrolysis furnace operated at 580° C. with a contact time of approximately 2 s. The pyrolysis effluent is quickly cooled to 45° C. and condenses into a liquid pyrolysis effluent. The non-condensed part, which constitutes the vapor pyrolysis effluent, comprises 97.5% by weight of 1,3-butadiene. The composition of the liquid pyrolysis effluent is indicated in Table 2.

TABLE 2

Composition by Mass and Molar Composition of the Liquid Pyrolysis Effluent.

|  | % by Mass | Mol % |
|---|---|---|
| AA | 79.60% | 83.54% |
| 2,3-BDOdiAc | 2.81% | 1.02% |
| BDE | 9.01% | 10.51% |
| VCH | 0.62% | 0.36% |
| MEK | 0.57% | 0.50% |
| MVCA | 0.95% | 0.52% |
| MEKEA | 3.49% | 1.93% |
| CA | 2.64% | 1.46% |
| MAA | 0.31% | 0.17% |

2,3-BDODiAc = 2,3-Butanediol Diacetate,
BDE = Butadiene,
VCH = Vinyl Cyclohexene,
MEK = Methyl Ethyl Ketone,
MAA = Methyl Acetylacetone,
MVCA = Methyl Vinyl Carbinol Acetate,
MEKEA = Methyl Ethyl Ketone Enol Acetate,
CA = Crotyl Acetate.

Two tests for esterification of 2,3-butanediol by acetic acid were carried out. One test was carried out with pure acetic acid, and the other was carried out with the liquid pyrolysis effluent described above. These tests were conducted in a batch reactor with a volume of 30 mL at atmospheric pressure, equipped with a condenser. The temperature is constant and regulated at 110° C. owing to a coolant in a double jacket. The reactions are performed in the presence of an Amberlyst 36 catalyst, with an H+ acid group number that is present at a concentration of 2.2 mol % in relation to the 2,3-butanediol. These reactions were carried out with an acetic acid/2,3-butanediol molar ratio of 6. These tests made it possible to monitor the kinetics of the esterification reaction, as well as the changes in the different impurities and intermediate pyrolysis compounds over time.

It is also noted by the results that are presented in the table below that the impurities that are present in the liquid pyrolysis effluent, some have changed over time.

TABLE 3

Results of the Two Tests for Esterification of 2,3-BDO with Pure Acetic Acid and with a Liquid Pyrolysis Effluent

|  | Acetic Acid $C^{initial}$ (mol · L$^{-1}$) | Pyrolysis Liquid $C^{final}$ (mol · L$^{-1}$) |
|---|---|---|
| BDE | 1.2551 | 1.2305 |
| VCH | 0.0864 | 0.0542 |
| MEK | 0.0794 | 0.6371 |
| MVCA | 0.1323 | 0.1407 |
| MEKEA | 0.4862 | 0.0117 |
| CA | 0.3678 | 0.2905 |
| MAA | 0.0432 | 0.0000 |

The concentrations of VCH and MVCA have not changed much. The CA also does not change significantly. In contrast, it is shown here that the MEKEA and the MAA disappear almost totally under the conditions of the esterification to provide the MEK. Actually, the disappearance of the MEKEA and MAA corresponds to 0.5177 mol·L$^{-1}$, and the formation of MEK corresponds to 0.5577 mol·L$^{-1}$, which is within the measurement error.

It is thus demonstrated that certain intermediate pyrolysis compounds and certain pyrolysis by-products are partially or totally converted into other products under the esterification conditions, which can be more easily separated from acetic acid, which makes it possible to prevent their accumulation. Thus, the concatenation of the esterification/pyrolysis steps with recycling of the liquid pyrolysis effluent according to the invention makes it possible—by the induced transformation of certain by-products—to improve the operation of the separation steps carried out on the carboxylic acid effluent.

Example 3 [Compliant] Elimination of the MEK, Pyrolysis By-Products Before Drying of the Acetic Acid by Heterogeneous Azeotropic Distillation This example shows that in the absence of a driver, the by-products contained in the carboxylic acid effluent can be separated by distillation by producing a carboxylic acid residue that comprises almost exclusively carboxylic acid and water, which residue can be easily treated by heterogeneous azeotropic distillation.

The table below shows the material balance in a distillation column, operated at atmospheric pressure, with 15 theoretical stages of balance, a reflux rate by mass of 1.48 and a reboiling rate by mass of 0.47, where the feeding is done in Stage 5.

TABLE 4

Material Balance in the Azeotropic Distillation Column for Elimination of the MEK (Step c)), Before Drying of the Acetic Acid by Heterogeneous Azeotropic Distillation (Step d)).

|  | Feed | Distillate | Residue |
|---|---|---|---|
| Temperature (° C.) | 94.7 | 83.4 | 99.6 |
| Mass Flow Rate |  |  |  |
| MEK | 0.106 | 0.105 | 0.001 |
| Acetic Acid | 1.000 | 0.030 | 0.970 |
| MVCA | 0.081 | 0.081 | 0.000 |
| CA | 0.108 | 0.078 | 0.030 |
| Water | 0.523 | 0.091 | 0.432 |
| VCH | 1.69E−05 | 1.69E−05 | 0.00E+00 |

The MEK is eliminated to 99%, the MVCA to 100%, the CA to 72%, the VCH to 100%, the water to 17%. This simulation reveals a loss in acetic acid of 3%, which is entirely acceptable.

The MEK-free residue can be distilled in an effective manner by heterogeneous azeotropic distillation.

Example 4 [Compliant] Elimination of the MEK, Pyrolysis By-Products Before Drying of Acetic Acid by Heterogeneous Azeotropic Distillation This example shows that in the absence of a driver, the by-products contained in the carboxylic acid effluent can be separated by distillation by producing a carboxylic acid residue that comprises almost exclusively carboxylic acid and water, which residue can easily be treated by heterogeneous azeotropic distillation. In this example, the column is operated in such a way that separation takes place in the condenser.

The table below shows the material balance in a distillation column, operated between 1 and 2 bar, with 25 theoretical stages of balance, a reflux rate by mass of 2.15, and a reboiling rate by mass of 0.9, where the feeding is done in Stage 13, knowing that the first stage is at the top of the column.

The vapors at the top of the column are condensed up to 86° C. and sent to a reflux tank in which two liquid phases coexist. The organic phase is drawn off as distillate and is free of acetic acid. The aqueous phase (with the composition of 96% by weight of water, 1.6% by weight of MEK, and 1.1% by weight of MVCA) is sent back as reflux to the distillation column.

TABLE 5

Material Balance in the Azeotropic Distillation Column for Elimination of the MEK, Before Drying of the Acetic Acid.

|  | Feed | Distillate | Residue |
|---|---|---|---|
| Temperature (° C.) | 96.6 | 86 | 114.5 |
| Mass Flow Rate |  |  |  |
| MEK | 0.02955 | 0.02955 | 0.00000 |
| MEKEA | 0.04677 | 0.04677 | 0.00000 |
| Acetic Acid | 1.00000 | 0.00003 | 0.99997 |
| MVCA | 0.15535 | 0.15535 | 0.00000 |
| CA | 0.08946 | 0.08946 | 0.00000 |
| Water | 0.57785 | 0.01618 | 0.56167 |
| VCH | 0.00003 | 0.00003 | 0.00000 |

The MEK is eliminated to 100%, the MVCA to 100%, the CA to 100%, the VCH to 100%, the water to 28%. This simulation reveals a loss in acetic acid of 0.003%, which is quite insignificant.

The residue that is free of MEK, CA, MVCA can be distilled in an effective manner by heterogeneous azeotropic distillation, and all of the acetic acid can thus be recovered so as to be recycled and upgraded.

Example 5 [Compliant] Elimination of the THF, Pyrolysis By-Products Before Drying of Acetic Acid by Heterogeneous Azeotropic Distillation This example shows that in the absence of a driver, the by-products contained in the carboxylic acid effluent can be separated by distillation by producing a carboxylic acid residue that comprises almost exclusively carboxylic acid and water, which residue can easily be treated by heterogeneous azeotropic distillation.

This example shows the simulation of the method for eliminating the THF and the pyrolysis by-products before the drying of the acetic acid by heterogeneous azeotropic distillation, according to the invention.

The table below shows the material balance in a distillation column, operated at atmospheric pressure, with 15 theoretical stages of balance, a reflux rate by mass of 10, and a reboiling rate by mass of 0.42, where the feeding is done in Stage 5.

TABLE 6

Material Balance in the Azeotropic Distillation Column for Elimination of the THF and the Pyrolysis By-Product, Before Drying of the Acetic Acid.

|  | Feed | Distillate | Residue |
|---|---|---|---|
| Temperature (° C.) | 94.7 | 83.4 | 99.6 |
| Mass Flow Rate |  |  |  |
| Acetic Acid | 1.0000 | 0.0185 | 0.9815 |
| MonoAc (=1.4) | 0.0869 | 0.0869 | 0.0000 |
| WATER | 1.2293 | 0.0374 | 1.1919 |
| THF | 1.21E−04 | 1.21E−04 | 1.61E−10 |
| VCH | 0.0024 | 0.0024 | 0.0000 |

The THF is eliminated to 100%, the monoacetyl obtained from pyrolysis is eliminated to 100%, the is also eliminated, VCH to 100%, water to 3%. This simulation reveals a loss in acetic acid of 2%, which is entirely acceptable.

The residue for the most part consists of water and acetic acid. Thus, this residue can be distilled in an effective manner by heterogeneous azeotropic distillation in the presence of a driver.

The invention claimed is:

1. A method for producing 1,3-butadiene from butanediol, which method comprises at least:
    a) esterifying the butanediol by a carboxylic acid in a mixture comprising the butanediol, the carboxylic acid and a liquid pyrolysis effluent, in a reactive distillation column, in the presence of a homogeneous or heterogeneous acid catalyst, and at a pressure of between 0.01 and 1 MPa to form the corresponding diester, thereby producing at least a carboxylic acid effluent and a diester effluent;
    b) pyrolyzing the diester effluent obtained from a) in a reaction section at a temperature of between 500° C. and 650° C. thereby producing a reaction-section effluent, cooling said reaction-section effluent to a temperature that is less than 100° C., and feeding the cooled reaction-section to a separation section and separating at least a liquid pyrolysis effluent comprising at least 50% by weight of carboxylic acid and a vapor pyrolysis effluent comprising more than 90% by weight of butadiene, said liquid pyrolysis effluent feeding the esterification in a);

c) distilling at least the carboxylic acid effluent obtained from a), in a distillation column at a pressure that is less than or equal to 1 MPa, at a temperature at the top of the column between 0 and 110° C. and a temperature at the bottom of the column between 100° C. and 120° C., and producing an aqueous distillate comprising the by-products of a) and b), and a carboxylicacid residue;

d) drying the carboxylic acid residue obtained from c) and producing a water effluent and a carboxylic acid recycle that is fed to esterification in a).

2. The method according to claim 1, in which said butanediol feedstock comprises at least 90% by weight of a butanediol that is 1,4-butanediol, 1,3-butanediol, or 2,3-butanediol, or a mixture thereof.

3. The method according to claim 1, in which said carboxylic acid is acetic acid.

4. The method according to claim 1, in which the reactive distillation of a) comprises a reaction/separation mixed zone located between two separation zones.

5. The method according to claim 4, in which said mixed zone comprises a heterogeneous acid catalyst that is an ion-exchange acid resin, a mixed oxide, or an acid zeolite.

6. The method according to claim 4, in which MMH, corresponding to the butane diol molar flow rate divided by the number of moles of catalyst present within said mixed zone, is between 0.05 and 25 h-1.

7. The method according to claim 1, wherein the reactive distillation column of step a) has a dwell time, defined as the volume of the reactive distillation column divided by the volumetric flow rate of butane-diol and carboxylic acid, between 0.5 h and 10 h.

8. The method according to claim 1, in which said liquid pyrolysis effluent of b) is purified before being recycled to step a) in a mixture with the carboxylic acid.

9. The method according to claim 1, in which said aqueous distillate of c) does not comprise more than 10% by weight of carboxylic acid.

10. The method according to claim 1, in which c) is operated in a distillation column at a temperature of the top of the column between 50° C. and 100° C., and a temperature of the bottom of the column between 100° C. and 115° C.

11. The method according to claim 1, in which d) is implemented by heterogeneous azeotropic distillation in the presence of a driver.

12. The method according to claim 11, in which said driver of d) is isopropyl acetate.

* * * * *